US006410773B1

(12) United States Patent
Yasohara et al.

(10) Patent No.: US 6,410,773 B1
(45) Date of Patent: Jun. 25, 2002

(54) SULFONIC ACID ESTER DERIVATIVES, METHOD FOR PRODUCTION THEREOF AND USE THEREOF

(75) Inventors: Yoshihiko Yasohara; Kenji Miyamoto; Shigeru Kawano; Junzo Hasegawa, all of Hyogo (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 09/512,281

(22) Filed: Feb. 24, 2000

Related U.S. Application Data

(62) Division of application No. 09/230,686, filed as application No. PCT/JP97/02699 on Aug. 1, 1997, now Pat. No. 6,121,477.

(30) Foreign Application Priority Data

Aug. 2, 1996 (JP) ............................................. 8-220344
Sep. 10, 1996 (JP) ............................................. 8-262398

(51) Int. Cl.$^7$ ........................................... C07C 311/00
(52) U.S. Cl. ........................... 558/44; 568/700; 568/715
(58) Field of Search ........................... 558/44; 568/700, 568/715

(56) References Cited

U.S. PATENT DOCUMENTS 3,840,579 A * 10/1974 Fan .............................. 558/54

FOREIGN PATENT DOCUMENTS

JP   62-502259   3/1987
JP   8-59606     3/1996

OTHER PUBLICATIONS

"Synthesis of Compound X, a Non–Steroidal Constituent of Female Urine, and Congeners", M.B. Groen and J. Leemhuis, pp. 5043–5046, 1980.

Journal of the American Chemical Society, vol. 16, No. 17, pp. 7475–7480, Aug. 24, 1994.

* cited by examiner

Primary Examiner—Paul J. Killos
Assistant Examiner—Taylor V OH
(74) Attorney, Agent, or Firm—Armstrong, Westerman, Hattori, McLeland & Naughton, LLP

(57) ABSTRACT

Novel and useful optical active 2-aralkyl-3-sulfonyloxy-1-propanol and 2-aralkyl-3-sulfonyloxypropionic acid are provided by using an optical active 2-aralkyl-3-acyloxy-1-propanol as a starting material. Furthermore, an optical active 2-aralkyl-3-thiopropionic acid, which is an important intermediate of enkephalinase inhibitor, is provided. According to the present invention, industrially useful optical active sulfonic acid ester derivatives can be provided.

13 Claims, No Drawings

SULFONIC ACID ESTER DERIVATIVES, METHOD FOR PRODUCTION THEREOF AND USE THEREOF

This application is a division of prior application Ser. No. 09/230,686, filed Jan. 29, 1999 now U.S. Pat. No. 6,121,477, which is a 371 of PCT/JP97/02699, filed Aug. 1, 1997.

TECHNICAL FIELD

The present invention relates to sulfonic acid ester derivatives, method for the production thereof and use thereof.

BACKGROUND ART

As lenitive medicines developed recently, an enkephalinase inhibitor is known. This inhibitor contains a structure derived from 2-aralkyl-3-thiopropionic acid. The stereospecificity of the 2-position of this structure is known to influence the expression of pharmaceutical action. For example, it is described in European Laid-Open Patent Publication EP-A-0,318,377 that, although both S-form and R-form of N-[2-(acetylthiomethyl)-1-oxo-3-phenyl-propyl] glycine benzyl ester have similar enkephalinase inhibition activities, the S-form has an inhibiting activity against an angiotensin converting enzyme which converts angiotensin I to angiotensin II and has an antihypertensive effect, while, the R-form can be used for therapy of intestinal function disease or intestinal hypersensitive syndrome.

As a method for preparing an optical active 2-aralkyl-3-acetylthiopropionic acid, Japanese Laid-Open Patent Publication No.8-59606 discloses optical resolution using ephedrine. However, the method for preparing an optical active 2-aralkyl-3-acetylthiopropionic acid directly by optical resolution is not economical, because agents for optical resolution are very expensive and the yield of the optical resolution is very low. On the other hand, an optical active 2-aralkyl-3-chloropropionic acid is considered as a precursor for optical active 2-aralkyl-3-thiopropionic acid. In Japanese Laid-Open Patent Publication No.7-316094, it is described that (S)-2-aralkyl-3-chloropropionic acid can be obtained by asymmetrically hydrogenating (S)-2-aralkylidene-3-chloropropionic acid using a complex of ruthenium and an optical active bidentate phosphine as a catalyst in the presence of a tertiary amine. However, this method does not appear to be economical because the catalyst is expensive and hydrogen pressure should be kept high in the reaction system. Furthermore, an optical purity of (S)-2-aralkyl-3-chloropropionic acid obtained by this method is unsatisfactory. It is described in Chemische. Berichte. vol.123, p635–638 (1990) that (R)-2-aralkyl-3-chloropropionic acid can be produced from L-phenylalanine by using 7-step process, including a step of a transfer reaction with a high temperature and a step of enzyme reaction by use of swine liver lipase. However, this method includes many steps of reaction and the transfer reaction with a high temperature which is difficult to practice industrially.

On the other hand, 2-aralkyl-3-sulfonyloxypropionic acid, which is a sulfonic acid ester derivative, is considered to be one of precursors of 2-aralkyl-3-thiopropionic acid. However, synthesis or isolation of racemic compounds or optical active compounds of 2-aralkyl-3-sulfonyloxypropionic acid has not been reported. Therefore, the above mentioned 2-aralkyl-3-sulfonyloxypropionic acid seems to be a novel compound and an industrially applicable producing method has not been established yet.

As stated above, although production methods of an optical active 2-aralkyl-3-thiopropionic acid that is an intermediate of the enkephalinase inhibitor are known, these methods do not seem to be industrially practical in that very expensive reagents are necessary, that industrially unpractical reaction conditions are included, and that optical purity of the product by these methods is low.

The present invention is to provide a novel sulfonic acid ester derivative, 2-aralkyl-3-sulfonyloxypropionic acid having the following general formula (3):

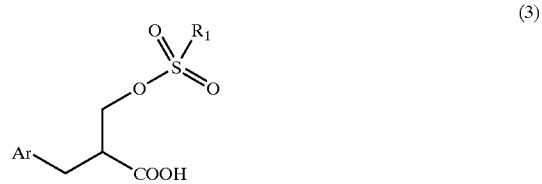

wherein Ar is an aryl group that may be substituted and $R_1$ is an alkyl group that may be substituted or an aryl group that may be substituted, an industrially advantageous producing method thereof and a method for producing 2-aralkyl-3-thiopropionic acid using the same.

DISCLOSURE OF INVENTION

In light of the above situation, after an extensive and intensive series of studies, the present inventors have found out that a novel optical active 2-aralkyl-3-sulfonyloxypropionic acid and a novel optical active 2-aralkyl-3-thiopropionic acid can be produced with high yield by using an optical active 2-aralkyl-3-acyloxy-1-propanol as a starting material and a using novel optical active 2-aralkyl-3-sulfonyloxy-1-propanol as an intermediate.

The present invention relates, in a first aspect, to an optical active 2-aralkyl-3-sulfonyloxy-1-propanol having the following general formula (1):

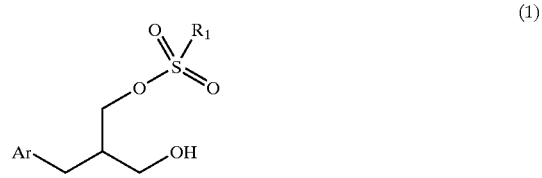

wherein Ar is an aryl group that may be substituted, and $R_1$ is methyl group, ethyl group, n-propyl group, isopropyl group, benzyl group, p-chlorophenyl group, p-bromophenyl group, p-methoxyphenyl group, o-nitrophenyl group, m-nitrophenyl group, p-nitrophenyl group or 1-naphthyl group.

The present invention relates, in a second aspect, to a method for producing an optical active 2-aralkyl-3-sulfonyloxy-1-propanol having the following general formula (1):

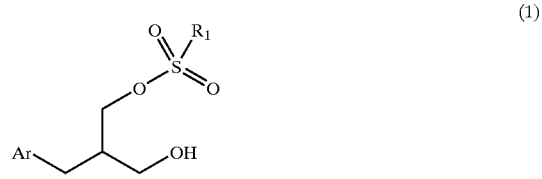

wherein Ar is an aryl group that may be substituted and $R_1$ is methyl group, ethyl group, n-propyl group, isopropyl group, benzyl group, p-chlorophenyl group, p-bromophenyl group, p-methoxyphenyl group, o-nitrophenyl group, m-nitrophenyl group, p-nitrophenyl group or 1-naphthyl group, which comprises hydrolyzing, in the presence of a base, an optical active 2-aralkyl-1-acyloxy-3-sulfonyloxypropane having the following general formula (2):

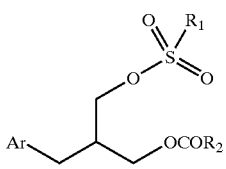
(2)

wherein Ar is an aryl group that may be substituted, $R_1$ is a methyl group, ethyl group, n-propyl group, isopropyl group, benzyl group, p-chlorophenyl group, p-bromophenyl group, p-methoxyphenyl group, o-nitrophenyl group, m-nitrophenyl group, p-nitrophenyl group or 1-naphthyl group and $R_2$ is a linear or branched alkyl group that may be substituted, a linear or branched alkenyl group that may be substituted or an aryl group that may be substituted.

The present invention relates, in a third aspect, to an optical active 2-aralkyl-3-sulfonyloxypropionic acid having the following general formula (3):

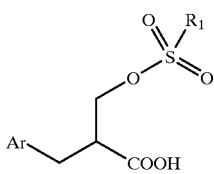
(3)

wherein Ar is an aryl group that may be substituted and $R_1$ is an alkyl group that may be substituted or an aryl group that may be substituted.

The present invention relates, in a fourth aspect, to a method for producing an optical active 2-aralkyl-3-sulfonyloxy-propionic acid having the following general formula (3):

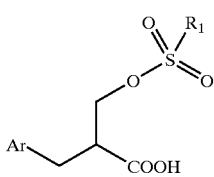
(3)

wherein Ar is an aryl group that may be substituted and $R_1$ is an alkyl group that may be substituted or an aryl group that may be substituted, which comprises oxidizing an optical active 2-aralkyl-3-sulfonyloxy-1-propanol having the following general formula (1):

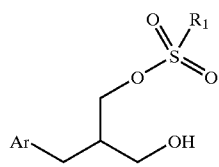
(1)

wherein Ar is an aryl group that may be substituted and $R_1$ is an alkyl group that may be substituted or an aryl group that may be substituted.

The present invention relates, in a fifth aspect, to a method for producing an optical active 2-aralkyl-3-sulfonyloxypropionic acid having the following general formula (3):

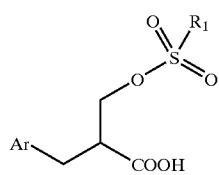
(3)

wherein Ar is an aryl group that may be substituted and $R_1$ is an alkyl group that may be substituted or an aryl group that may be substituted, which comprises reacting an optical active 2-aralkyl-3-hydroxypropionic acid having the following general formula (4):

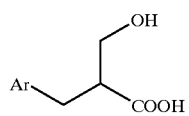
(4)

wherein Ar is an aryl group that may be substituted, with a sulfonic acid halide having the following general formula (5):

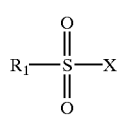
(5)

wherein $R_1$ is an alkyl group that may be substituted or an aryl group that may be substituted and X is a halogen atom.

The present invention relates, in a sixth aspect, to a method for producing an optical active 2-aralkyl-3-thiopropionic acid having the following general formula (8):

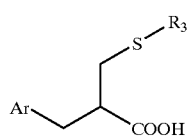
(8)

wherein Ar is an aryl group that may be substituted and $R_3$ is an alkyl group that may be substituted, an acyl group that may be substituted or an aryl group that may be substituted, which comprises reacting an optical active 2-aralkyl-3-sulfonyloxy-propionic acid having the following general formula (3):

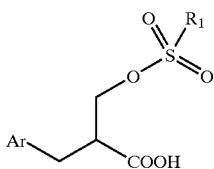
(3)

wherein Ar is an aryl group that may be substituted and $R_1$ is an alkyl group that may be substituted or an aryl group that may be substituted, with a thio-compound having the following general formula (7):

(7)

wherein $R_3$ is an alkyl group that may be substituted, an acyl group that may be substituted or an aryl group that may be substituted and Y is a hydrogen atom or an alkali metal atom.

BEST MODE FOR CARRYING OUT THE INVENTION

In the first invention, as Ar, a phenyl group that may be substituted or a naphthyl group that may be substituted is preferable. A phenyl group that may be substituted with alkyl group, substituted alkyl group, alkoxy group, substituted alkoxy group or halogen atom is more preferable, and phenyl group is the most preferable.

As $R_1$, methyl group is preferable. Especially, Ar being phenyl group and $R_1$ being methyl group is preferable.

From the second to sixth inventions, as Ar, a phenyl group that may be substituted or a naphthyl group that may be substituted is preferable. A phenyl group that may be substituted with alkyl group, substituted alkyl group, alkoxy group, substituted alkoxy group or halogen atom is more preferable, and phenyl group is the most preferable.

As $R_1$, methyl group, ethyl group, n-propyl group, isopropyl group, benzyl group, phenyl group, p-methylphenyl group, p-chlorophenyl group, p-bromophenyl group, p-methoxyphenyl group, o-nitrophenyl group, m-nitrophenyl group, p-nitrophenyl group or 1-naphthyl group is preferable and methyl group is more preferable. Especially, Ar being phenyl group and $R_1$ being methyl group is preferable.

An optical active 2-aralkyl-3-acyloxy-1-propanol which is a starting material of a novel compound of the present invention has the following general formula (6):

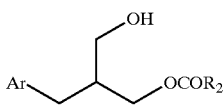
(6)

wherein Ar is an aryl group that may be substituted and $R_2$ is a linear or branched alkyl group that may be substituted, a linear or branched alkenyl group that may be substituted or an aryl group that may be substituted.

The compound can be obtained, for example, according to a method described in Tetrahedron Letters vol.31, p1601 (1990). That is, the compound can be obtained by reacting 2-aralkyl-1,3-propanediol, in the presence of a acylating agent, with an enzyme which is able to stereoselectively esterify hydroxyl group of either 1- or 3-position. In another method, the compound can be obtained by reacting 2-aralkyl-1,3-diacyloxypropane with an enzyme that is able to hydrolyze an ester of either 1- or 3-position.

Then, the optical active 2-aralkyl-3-acyloxy-1-propanol expressed by above general formula (6) obtained as described above is reacted with a sulfonic acid halide having the following general formula (5):

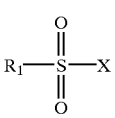
(5)

wherein $R_1$ is methyl group, ethyl group, n-propyl group, isopropyl group, benzyl group, p-chlorophenyl group, p-bromophenyl group, p-methoxyphenyl group, o-nitrophenyl group, m-nitrophenyl group, p-nitrophenyl group or 1-naphthyl group, and X is a halogen atom, in the presence of a base, so as to obtain an optical active 2-aralkyl-1-acyloxy-3-sulfonyloxypropane having the following general formula (2):

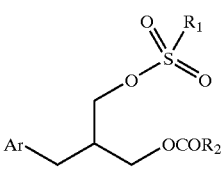
(2)

wherein Ar is an aryl group that may be substituted, $R_1$ is methyl group, ethyl group, n-propyl group, isopropyl group, benzyl group, p-chlorophenyl group, p-bromophenyl group, p-methoxyphenyl group, o-nitrophenyl group, m-nitrophenyl group, p-nitrophenyl group or 1-naphthyl group and $R_2$ is a linear or branched alkyl group that may be substituted, a linear or branched alkenyl group that may be substituted or an aryl group that may be substituted.

This reaction can be conducted in a non-organic solvent system. However, it is preferable to conduct it in an organic solvent, for example, alcohols such as methanol, ethanol and isopropyl alcohol, halogenated hydrocarbons such as methylene chloride, chloroform and carbon tetrachloride, aromatic hydrocarbons such as benzene, toluene and xylene, ethers such as diethyl ether, tetrahydrofuran and diisopropyl ether, hydrocarbons such as pentane and hexane, acetonitrile, dimethyl sulfoxide, acetone and ethyl acetate. The above solvents can be used alone or in combination of two or more.

As the base, amines such as triethylamine, trimethylamine, diisopropylethylamine, N,N-dimethylaniline and N,N-diethylaniline, aromatic nitrogen compounds such as pyridine, 4-(N,N-dimethylamino) pyridine, imidazole and 2,6-lutidine, or sodium ethoxide, sodium-methoxide, potassium tertiary butoxide, sodium hydride, potassium hydride, calcium carbonate, potassium carbonate, sodium carbonate, lithium carbonate, potassium hydrogen carbonate, sodium hydrogen carbonate, sodium hydroxide, and potassium hydroxide can be exemplified. These bases can be used alone or in combination of two or more.

The amount of the sulfonic acid halide to be used is preferably 1.0 equivalent or more with respect to a substrate, compound expressed by the general formula (6). If the amount is less than 1.0 equivalent, the efficiency of the reaction is apt to be decreased since all of the raw materials are not reacted. The amount of the base to be used is about equivalent molar with respect to the sulfonic acid halide. The reaction can be conducted in a wide range of temperature, however, usually, a temperature from $-10°$ C. to $100°$ C. is preferable. If the temperature is out of this range, the efficiency of the reaction is apt to be lowered. After the reaction has been completed, the aimed product can be obtained easily by adding water to the reaction mixture, followed by extracting with an organic solvent such as toluene and ethyl acetate and removing the solvent. If necessary, the product can be highly purified using silica gel column chromatography and so on.

Then, the thus obtained optical active 2-aralkyl-1-acyloxy-3-sulfonyloxypropane expressed by the general formula (2) is added to an organic solvent and methanol containing a strong base or an aqueous solution containing a strong base, and hydrolyzed so as to an obtain optical active 2-aralkyl-3-sulfonyloxy-1-propanol having the following general formula (1):

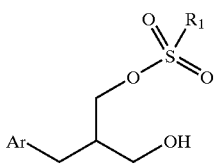

(1)

wherein Ar is an aryl group that may be substituted and $R_1$ is methyl group, ethyl group, n-propyl group, isopropyl group, benzyl group, p-chlorophenyl group, p-bromophenyl group, p-methoxyphenyl group, o-nitrophenyl group, m-nitrophenyl group, p-nitrophenyl group or 1-naphthyl group.

As the organic solvent, alcohols such as methanol, ethanol and isopropyl alcohol, halogenated hydrocarbons such as methylene chloride, chloroform and carbon tetrachloride, aromatic hydrocarbons such as benzene, toluene and xylene, ethers such as diethyl ether, tetrahydrofuran and diisopropyl ether, hydrocarbons such as pentane and hexane, acetonitrile, dimethyl sulfoxide, acetone and ethyl acetate are preferable. The above solvents can be used alone or in combination of two or more.

As the strong base, for example, sodium hydroxide and potassium hydroxide are preferable. These bases can be used alone or in combination of two or more. After the reaction has been completed, the aimed product can be obtained easily by extracting with an organic solvent such as toluene and ethyl acetate, followed by removing the solvent. If necessary, the product can be highly purified using silica gel column chromatography and so on.

Then, as described in J. Org. Chem. Vol.52, p25559 (1987), by oxidizing the hydroxyl group of the thus obtained optical active 2-aralkyl-3-sulfonyloxy-1-propanol having the general formula (1) or a known compound of 2-aralkyl-3-sulfonyloxy-1-propanol having the general formula (1) in which Ar is phenyl group and $R_1$ is phenyl group or p-methylphenyl group, or in which Ar is 3-methoxyphenyl group and $R_1$ is p-methylphenyl group, an optical active 2-aralkyl-3-sulfonyloxypropionic acid having the following general formula (3) can be obtained:

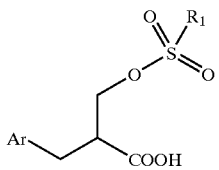

(3)

wherein Ar is an aryl group that may be substituted and $R_1$ is an alkyl group that may be substituted or an aryl group that may be substituted.

That is, using one or more of 2,2,6,6-tetramethylpiperidine-1-oxy or 4-substituted 2,2,6,6-tetramethylpiperidine-1-oxy derivative, for example, 4-methoxy-2,2,6,6-tetramethylpiperidine-1-oxy, 4-hydroxy-2,2,6,6-tetramethylpiperidine-1-oxy, 4-benzoyloxy-2,2,6,6-tetramethylpiperidine-1-oxy, 4-amino-2,2,6,6-tetramethylpiperidine-1-oxy and 4-oxo-2,2,6,6-tetramethylpiperidine-1-oxy as a catalyst, in a binary phase system comprised of an organic phase including potassium bromide and a phase transfer catalyst and a water phase, the compound having the general formula (3) can be easily obtained by reacting a compound having the general formula (1) with sodium hypochlorite, followed by extracting, in an acidic condition, with an organic solvent such as toluene and ethyl acetate and removing the solvent. If necessary, the product can be highly purified using silica gel column chromatography and so on.

The optical active 2-aralkyl-3-sulfonyloxypropionic acid having the following general formula (3):

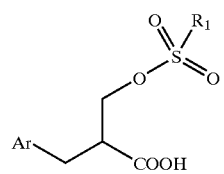

(3)

wherein Ar is an aryl group that may be substituted and $R_1$ is an alkyl group that may be substituted or an aryl group that may be substituted, can be also obtained by the method described below:

Starting material of this method, optical active 2-aralkyl-3-hydroxypropionic acid having the following general formula (4):

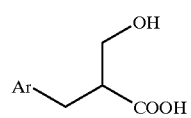

(4)

wherein Ar is an aryl group that may be substituted, can be obtained by the method described in Tetrahedron Letters vol.31, p1601 (1990).

That is, by reacting 2-aralkyl-1,3-propanediol, in the presence of an acylating agent, with an enzyme which is able to stereoselectively esterify hydroxyl group of either 1- or 3-position or by reacting 2-aralkyl-1,3-diacyloxypropane with an enzyme which is able to hydrolyze an ester of either 1- or 3-position, an optical active 2-aralkyl-3-acyloxy-1-propanol having the following general formula (6):

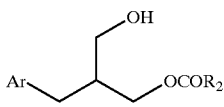

(6)

wherein Ar is an aryl group that may be substituted and $R_2$ is a linear or branched alkyl group that may be substituted, a linear or branched alkenyl group that may be substituted or an aryl group that may be substituted, can be prepared, and then by oxidizing the hydroxyl group of the compound having general formula (6) using a suitable method, an optical active 2-aralkyl-3-acyloxypropionic acid having the following general formula (9):

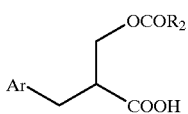

(9)

wherein Ar is an aryl group that may be substituted and $R_2$ is a linear or branched alkyl group that may be substituted, a linear or branched alkenyl group that may be substituted or an aryl group that may be substituted, can be prepared, then, by hydrolyzing the ester having the general formula (9), an optical active 2-aralkyl-3-hydroxypropionic acid having the following general formula (4):

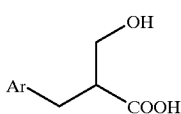

(4)

wherein Ar is an aryl group that may be substituted, can be obtained.

Then, in the presence of a base, the thus obtained optical active 2-aralkyl-3-hydroxypropionic acid having the general formula (4) is reacted with a sulfonic acid halide having the following general formula (5):

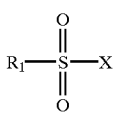

(5)

wherein $R_1$ is an alkyl group that may be substituted or an aryl group that may be substituted and X is a halogen atom, so as to obtain an optical active 2-aralkyl-3-sulfonyloxypropionic acid having the following general formula (3):

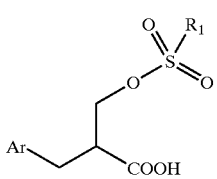

(3)

wherein Ar is an aryl group that may be substituted and $R_1$ is an alkyl group that may be substituted or an aryl group that may be substituted.

This reaction can be conducted in a non-organic solvent system, however, it is preferable to conduct it in an organic solvent, for example, alcohols such as methanol, ethanol and isopropyl alcohol, halogenated hydrocarbons such as methylene chloride, chloroform and carbon tetrachloride, aromatic hydrocarbons such as benzene, toluene and xylene, ethers such as diethyl ether, tetrahydrofuran and diisopropyl ether, hydrocarbons such as pentane and hexane, acetonitrile, dimethyl sulfoxide, acetone and ethyl acetate. The above solvents can be used alone or in combination of two or more.

As the base, amines such as triethylamine, trimethylamine, diisopropylethylamine, N,N-dimethylaniline and N,N-diethylaniline, aromatic nitrogen compounds such as pyridine, 4-(N,N-dimethylamino) pyridine, imidazole and 2,6-lutidine, or sodium ethoxide, sodium methoxide, potassium tertiary butoxide, sodium hydride, potassium hydride, calcium carbonate, potassium carbonate, sodium carbonate, lithium carbonate, potassium hydrogen carbonate, sodium hydrogen carbonate can be exemplified. The above bases can be used alone or in combination of two or more.

The amount of the sulfonic acid halide to be used is preferably 1.0 equivalent or more with respect to a substrate, compound having the general formula (4). If the amount is less than 1.0 equivalent, the efficiency of the reaction is apt to be decreased since all of the raw materials are not be reacted. The amount of the base to be used is about equivalent molar with respect to the sulfonic acid halide. The reaction can be conducted in a wide range of temperature, however, usually, a temperature from −10° C. to 100° C. is preferable. If the temperature is out of this range, the efficiency of the reaction is apt to be lowered. After the reaction has been completed, the aimed product can be obtained easily by adding water to the reaction mixture, followed by extracting with an organic solvent such as toluene and ethyl acetate and removing the solvent. If necessary, the product can be highly purified using such as silica gel column chromatography and so on.

Next, by reacting the thus obtained optical active 2-aralkyl-3-sulfonyloxypropionic acid with a thio-compound having the following general formula (7):

$$R_3-S-Y \quad (7)$$

wherein $R_3$ is an alkyl group that may be substituted, an acyl group that may be substituted or an aryl group that may be substituted and Y is a hydrogen atom or an alkali metal atom, an optical active 2-aralkyl-3-thiopropionic acid having the following general formula (8):

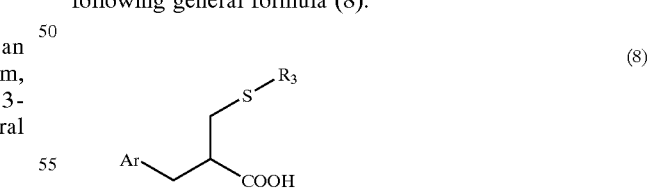

(8)

wherein Ar is an aryl group that may be substituted and $R_3$ is an alkyl group that may be substituted, an acyl group that may be substituted or an aryl group that may be substituted, can be obtained.

This reaction can be conducted in a non-organic solvent system, however, it is preferable to conduct it in organic solvent, for example, alcohols such as methanol, ethanol and isopropyl alcohol, halogenated hydrocarbons such as methylene chloride, chloroform and carbon tetrachloride, aromatic hydrocarbons such as benzene, toluene and xylene, ethers such as diethyl ether, tetrahydrofuran and diisopropyl ether, hydrocarbons such as pentane and hexane, acetonitrile, dimethyl sulfoxide, acetone and ethyl acetate. The above solvents can be used alone or in combination of two or more. A base may be added, if necessary.

As the base, amines such as triethylamine, trimethylamine, diisopropylethylamine, N,N-dimethylaniline and N,N-diethylaniline, aromatic nitrogen compounds such as pyridine, 4-(N,N-dimethylamino) pyridine, imidazole and 2,6-lutidine, or sodium ethoxide, sodium methoxide, potassium tertiary butoxide, sodium hydride, potassium hydride, calcium carbonate, potassium carbonate, sodium carbonate, lithium carbonate, potassium hydrogen carbonate, sodium hydrogen carbonate can be exemplified. The above bases can be used alone or in combination of two or more.

The reaction can be conducted in a wide range of temperature, however, usually, a temperature from −10° C. to 100° C. is preferable. If the temperature is out of this-range, the efficiency of the reaction is apt to be lowered. After the reaction has been completed, the aimed product can be obtained easily by extracting with an organic solvent such as toluene and ethyl acetate and removing the solvent. If necessary, the product can be highly purified using silica gel column chromatography and so on.

Hereinafter, the present invention will be explained in greater detail by way of Examples, however, the present invention will not be limited to these Examples.

REFERENCE EXAMPLE 1
Production of 2-benzylmalonic Acid Diethyl Ester

In 200 ml of ethanol, 16.2 g of sodium methoxide were dissolved. Into this solution, 49.5 g of diethyl malonate were dropped and gently refluxed. 37.98 g of benzyl chloride were dropped into the mixture over one hour and the mixture was refluxed for 2 hours. After the reaction was completed, the solvent was removed under reduced pressure, and water was added to the residue. After extraction with ethyl acetate, the ethyl acetate was dried with sodium sulfate anhydride. After removing the solvent under reduced pressure, followed by purification with distillation, 50 g of 2-benzylmalonic acid diethyl ester were obtained.

REFERENCE EXAMPLE 2
Production of 2-[[(3,4-methylenedioxy)phenyl]methyl]malonic Acid Diethyl Ester 60.17 g of sodium ethoxide were dissolved in 1127 ml of ethanol. To this solution, 336.4 g of diethyl malonate and 119.42 g of [(3,4-methylendioxy)phenyl]methyl chloride were added and the mixture was refluxed for 3 hours. After the reaction was completed, the solvent was removed under reduced pressure and water was added to the residue. After extraction with ethyl acetate, the ethyl acetate was dried with sodium sulfate anhydride. After removing the solvent under reduced pressure and purification with distillation, 181.1 g of 2-[[(3,4-methylenedioxy)phenyl]methyl]malonic acid diethyl ester were obtained.

REFERENCE EXAMPLE 3
Production of 2-[(4-Chlorophenyl)methyl]malonic Acid Diethyl Ester 60.17 g of sodium ethoxide were dissolved in 1127 ml of ethanol. To this solution, 336.4 g of diethyl malonate and 115.0 g of (4-chlorophenyl) methyl chloride were added and the mixture was refluxed for 2 hours. After the reaction was completed, the solvent was removed under reduced pressure and water was added to the residue. After extraction with ethyl acetate, the ethyl acetate was dried with sodium sulfate anhydride. After removing the solvent under reduced pressure and purification with distillation, 172.6 g of 2-[(4-chlorophenyl)methyl]malonic acid diethyl ester were obtained.

REFERENCE EXAMPLE 4
Production of 2-benzyl-1,3-propanediol 7.59 g of lithium aluminum hydride were suspended in 100 ml of tetrahydrofuran. Into this suspension, 70 ml of tetrahydrofuran solution containing 25.0 g of 2-benzylmalonic acid diethyl ester which was obtained in Reference example 1 were dropped under ice cooling, and then stirred for 1 hour under ice cooling and for 3 hours at room temperature. To this reaction solution, 200 ml of a 2N hydrogen chloride solution were added, then a tetrahydrofuran layer and a water layer were separated. To the water layer, ethyl acetate was added and the ethyl acetate layer was recovered. The obtained tetrahydrofuran layer and the ethyl acetate layer were mixed. After washing this mixture with a saturated sodium hydrogen carbonate aqueous solution and a saturated sodium chloride aqueous solution, the mixture was dried with sodium sulfate anhydride. After the solvent was removed under reduced pressure, 13.7 g of colorless and solid 2-benzyl-1,3-propanediol were re-crystallized from ethyl acetate-hexane.

$^1$H-NMR (400 MHz, CDCl$_3$) δ ppm: 2.00~2.11 (m, 1H), 2.32 (br s, 2H), 2.64 (d, J=7.8 Hz, 2H), 3.67 (dd, J1=6.8 Hz, J2=10.5 Hz, 2H), 3.81 (dd, J1=3.9 Hz, J2=10.5 Hz, 2H), 7.12~7.34 (m, 5H).

REFERENCE EXAMPLE 5
Production of 2-[[(3,4-methylenedioxy)phenyl]methyl]-1,3-propanediol 49.6 g of sodium borohydride were suspended into 500 ml of toluene. To this solution, 340 ml of toluene solution containing 173.7 g of 2-[[(3,4-methylenedioxy)phenyl]methyl]malonic acid diethyl ester obtained in Reference example 2 were added under ice cooling. To this solution, under ice cooling, 151.23 g of methanol were dropped, and stirred for 1 hour under cooling and overnight at room temperature. The thus obtained solution was added to 200 ml of a 2N sulfuric acid and the pH of the solution was adjusted to 9 using a 6N sodium hydroxide aqueous solution. After deposited salt was removed by filtration, a toluene layer and a water layer were separated. To the water layer, ethyl acetate was added and the ethyl acetate layer was recovered. The toluene layer and the ethyl acetate layer were mixed, and the mixture was washed with a saturated sodium chloride aqueous solution, and dried with sodium sulfate anhydride. The solvent was removed under reduced pressure and 99.7 g of colorless and solid 2-[[(3,4-methylenedioxy)phenyl]methyl]-1,3-propanediol was crystallized from ethyl acetate-n-hexane.

$^1$H-NMR (400 MHz, CDCl$_3$) δ ppm 1.95~2.05 (m, 1H), 2.10 (br s, 2H), 2.55 (d, J=7.8 Hz, 2H), 3.66 (dd, J1=6.8 Hz, J2=10.3 Hz, 2H), 3.80 (dd, J1=3.7 Hz, J2=10.5 Hz, 2H), 5.93 (s, 2H), 6.63 (dd, J1=1.5 Hz, J2=7.8 Hz, 1H), 6.67 (d, J=1.5 Hz, 1H), 6.73 (d, J=7.8 Hz, 1H).

REFERENCE EXAMPLE 6
Production of 2-[(4-Chlorophenyl)methyl]-1,3-propanediol 49.6 g of sodium borohydride were suspended into 500 ml of toluene. To this solution, 340 ml of toluene solution containing 168.0 g of 2-(4-chlorophenyl)methyl]malonic acid diethyl ester obtained in Reference example 3 were added under ice cooling. To this solution, under ice cooling, 151.23 g of methanol was dropped and stirred for 1 hour under cooling and overnight at room temperature. The thus obtained solution was added to 200 ml of a 2N sulfuric acid and the pH of the solution was adjusted to 9 using a 6N sodium hydroxide aqueous solution. After deposited salt was removed by filtration, a toluene layer and a water layer were separated. To the water layer, ethyl acetate was added and the ethyl acetate layer was recovered. The toluene layer and the ethyl acetate layer were mixed, and the mixture was washed with a saturated sodium chloride aqueous solution, and dried with sodium sulfate anhydride. The solvent was removed under reduced pressure and 101.8 g of colorless and solid 2-[(4-chlorophenyl)methyl]-1,3-propanediol was crystallized from ethyl acetate-n-hexane.

$^1$H-NMR (400 MHz, CDCl$_3$) δ ppm: 1.95~2.07 (m, 1H), 2.43 (br s, 2H), 2.61 (d, J=7.3 Hz, 2H), 3.65 (dd, J1=6.8 Hz, J2=10.8 Hz, 2H), 3.79 (dd, J1=3.9 Hz, J2=10.7 Hz, 2H), 7.12 (d. J=8.3 Hz, 2H), 7.26 (d, J=8.3 Hz, 2H).

REFERENCE EXAMPLE 7
Production of (R)-2-benzyl-3-acetyloxy-1-propanol

To 83 ml of toluene, 8.31 g of 2-benzyl-1,3-propanediol obtained in Reference example 4 were dissolved. To this solution, 8.61 g of vinyl acetate and 416 mg of lipase PS (manufactured by AMANO PHARMACEUTICAL CO., LTD.) were added and stirred for 16 hours at room temperature. After the reaction was terminated, the enzyme was removed by filtration and the solvent was removed under reduced pressure. The residue was purified by silica gel column chromatography (n-hexane: ethyl acetate 1:1) so as to obtain 9.82 g of (R)-2-benzyl-3-acetyloxy-1-propanol.

1H-NMR (400 MHz, CDCl$_3$) δ ppm: 2.01 (br s, 1H), 2.09 (S, 3H), 2.10~2.18 (m, 1H), 2.63 (dd, J1=7.8 Hz, J2=13.7 Hz, 1H), 2.69 (dd, J3=7.3 Hz, J2=13.7 Hz, 1H), 3.46~3.55 (m, 1H), 3.57~3.66 (m, 1H), 4.08 (dd, J4=6.4 Hz, J5=11.1 Hz, 1H), 4.19 (dd, J6=4.4 Hz, J5=11.1 Hz, 1H), 7.16~7.34 (m, 5H); Optical purity: 98.5% e.e.

The optical purity of 2-benzyl-3-acetyloxy-1-propanol was determined by the following HPLC conditions:

Column; CHIRALCEL OD (0.45 mm×25 cm)

Eluant; n-hexane.: 2-propanol=25:1

Wave length for detection; 254 nm

Elution rate; 0.5 ml/min.

Column temperature; room temperature

Elution time; (R)form;36.8 min., (S)form;40.0 min.

REFERENCE EXAMPLE 8
Production of (S)-2-benzyl-3-acetyloxy-1-propanol

To 10 ml of pyridine, 2.00 g of 2-benzyl-1,3-propanediol obtained in Reference example 4 were dissolved. To this solution, 10 mg of 4-dimethylaminopyridine were added. Under ice cooling, 3.68 g of acetic anhydride were dropped and stirred for 3 hours at room temperature. After the reaction was completed, ethyl acetate was added, followed by washing with a 1N hydrogen chloride, a saturated sodium hydrogen carbonate aqueous solution and a saturated sodium chloride aqueous solution. The solvent was dried with sodium sulfate anhydride. The solvent was removed under reduced pressure, followed by purifying the residue with silica gel column chromatography (n-hexane: ethyl acetate= 5:1), thereby obtaining 2.98 g of 2-benzyl-1,3-diacetyloxypropane.

$^1$H-NMR (400 MHz, CDCl$_3$) δ ppm: 2.06 (s, 6H), 2.28~2.40 (m, 1H), 2.70 (d, J1=7.3 Hz, 2H), 4.02 (dd, J1=5.9 Hz, J2=11.2 Hz, 2H), 4.08 (dd, J3=1.9 Hz, J2=11.2 Hz, 2H), 7.12~7.32 (m, 5H).

To 1.5 L of a 10 mM acetate buffer (pH5.0), 30.0 g of 2-benzyl-1,3-diacetyloxypropane obtained as above were suspended and the pH of the suspension was adjusted to 5.0 with a 6N sodium hydroxide aqueous solution with stirring at 20° C. To this suspension, 3.0 g of lipase P (manufactured by AMANO PHARMACEUTICAL CO., LTD.) were added and stirred at 20° C. for 17 hours with adjusting the pH constant using a pH automatic titrator. After the reaction was completed, sodium chloride was added to the solution so that the sodium chloride was saturated. The reaction mixture was extracted with ethyl acetate. The solvent was washed with a saturated sodium hydrogen carbonate aqueous solution and a saturated sodium chloride aqueous solution, followed by drying with sodium sulfate anhydride. The solvent was removed under reduced pressure and a residue was purified with silica gel column chromatography (n-hexane: ethyl acetate=5:1) so as to obtain 10.4 g of (S)-2-benzyl-3-acetyloxy-1-propanol. Optical purity of the obtained (S)-2-benzyl-3-acetyloxy-1-propanol was determined in the same manner as described in Reference example 7.

Optical purity: 98.3% e.e.

REFERENCE EXAMPLE 9
Production of (R)-2-[[(3,4-methylenedioxy)phenyl]methyl]-3-acetyloxy-1-propanol To 126 ml of toluene, 63.07 g of 2-[[(3,4-methylenedioxy)phenyl]methyl]-1,3-propanediol obtained in Reference example 5 were dissolved. To this solution, 31.31 g of vinyl acetate and 1.27 g of lipase PS (manufactured by AMANO PHARMACEUTICAL CO., LTD.) were added, followed by stirring for 17 hours at room temperature. After the reaction was completed, the enzyme was removed by filtration and the solvent was removed under reduced pressure so as to obtain 71.90 g of (R)-2-[[(3,4-methylenedioxy)phenyl]methyl]-3-acetyloxy-1-propanol.

$^1$H-NMR (400 MHz, CDCl$_3$) δ ppm: 1.95 (br s, 1H), 1.98~2.05 (m, 1H), 2.09 (s, 3H), 2.58 (dd, J1=7.3 Hz, J2=13.7 Hz, 2H), 3.50 (dd, J1=6.4 Hz, J2=11.2 Hz, 1H), 3.59 (dd, J1=4.4 Hz, J2=11.2 Hz, 1H), 4.06 (dd, J1=6.4 Hz, J2=11.2 Hz, 1H), 4.18 (dd, J1=4.9 Hz, J2=11.2 Hz, 1H), 5.90 (S, 2H), 6.63 (dd, J1=1.5 Hz, J2=7.8 Hz, 1H), 6.68 (S, 1H), 6.73 (d, J=7.8 Hz, 1H); Optical purity: 96.3% e.e.

The optical purity of 2-[[(3,4-methylenedioxy)phenyl]methyl]-3-acetyloxy-1-propanol was determined by the following HPLC conditions:

Column; CHIRALCEL OD (0.45 mm×25 cm)

Eluant; n-hexane: 2-propanol=9:1

Wave length for detection; 254 nm

Elution rate; 0.5 ml/min.

Column temperature; room temperature

Elution time; (R)form;21.7 min., (S)form;25.7 min.

REFERENCE EXAMPLE 10
Production of (R)-2-[(4-chlorophenyl)methyl]-3-acetyloxy-1-propanol To 120.3 ml of toluene, 60.19 g of 2-[(4-chlorophenyl)methyl]-1,3-propanediol obtained in Reference example 6 were dissolved. To this solution, 31.31 g of vinyl acetate and 1.20 g of lipase PS (manufactured by AMANO PHARMACEUTICAL CO., LTD) were added, followed by stirring for 18 hours at room temperature. After the reaction was completed, the enzyme was removed by filtration and the solvent was removed under reduced pressure so as to obtain 69.20 g of (R)-2-[(4-chlorophenyl)methyl]-3-acetyloxy-1-propanol.

$^1$H-NMR (400 MHz, CDCl$_3$) δ ppm: 1.90 (br s, 1H), 2.00~2.15 (m, 1H), 2.08 (s, 3H), 2.59 (dd, J1=7.3 Hz, J2=13.7 Hz, 1H), 2.68 (dd, J1=7.8 Hz, J2=13.7 Hz, 1H), 3.49

(dd, J1=6.4 Hz, J2=11.2 Hz, 1H), 3.59 (dd, J1=4.4 Hz, J2=11.2 Hz, 1H), 4.07 (dd, J1=6.4 Hz, J2=11.2 Hz, 1H), 4.17 (dd, J1=4.9 Hz, J2=11.2 Hz, 1H), 7.12 (d, J=8.3 Hz, 2H), 7.26 (d, J=8.3 Hz, 2H); Optical purity: 98.4% e.e.

The optical purity of 2-[(4-chlorophenyl)methyl]-3-acetyloxy-1-propanol was determined by the following HPLC conditions:

Column; CHIRALCEL OD (0.45 mm×25 cm)

Eluant; n-hexane: 2-propanol=9:1

Wave length for detection; 254 nm

Elution rate; 0.5 ml/min.

Column temperature; room temperature

Elution time; (R)form;15.2 min., (S)form;17.3 min.

REFERENCE EXAMPLE 11

Production of (S)-2-benzyl-1-acetyloxy-3-methanesulfonyloxypropane

To 100 ml of toluene, 10.41 g of (R)-2-benzyl-3-acetyloxy-1-propanol obtained in Reference example 7 were dissolved. Under ice cooling, 6.07 g of triethylamine were added. Then, 6.30 g of methanesulfonyl chloride were dropped into the solution and stirred for 1 hour. After the reaction was completed, ethyl acetate was added to the reaction mixture, followed by washing with a 1N hydrogen chloride, a saturated sodium hydrogen carbonate aqueous solution and a saturated sodium chloride aqueous solution, and dried with sodium sulfate anhydride. The solvent was removed under reduced pressure and the residue was purified with silica gel column chromatography (n-hexane: ethyl acetate=2:3) so as to obtain 13.60 g of (S)-2-benzyl-1-acetyloxy-3-methanesulfonyloxypropane.

$^1$H-NMR (400 MHz, CDCl$_3$) δ ppm: 2.13 (s, 3H), 2.40~2.50 (m, 1H), 2.79(d, 2H), 3.05(s, 3H), 4.10(dd, J1=6.8 Hz, J2=11.7 Hz, 1H), 4.16~4.23 (m, 2H), 4.28(dd, J3=4.9 Hz, J4=9.8 Hz, 1H), 7.18~7.39(m, 5H); Optical purity: 98.5% e.e.

The optical purity of 2-benzyl-1-acetyloxy-3-methanesulfonyloxypropane was determined by the following HPLC conditions:

Column: CHIRALCEL OD(0.45 mm×25 cm)

Eluant; n-hexane: 2-propanol=9:1

Wave length for detection; 254 nm

Elution rate; 0.5 ml/min.

Column temperature; room temperature

Elution time; (R)form;46.0 min.,(S)form;42.5 min.

REFERENCE EXAMPLE 12

Production of (S)-2-[[(3,4-methylenedioxy)phenyl]methyl]-1-acetyloxy-3-methanesulfonyloxypropane To 630.7 ml of toluene, 63.07 g of (R)-2-[[(3,4-methylenedioxy)phenyl]methyl]-3-acetyloxy-1-propanol obtained in Reference example 9 were dissolved. Under ice cooling, 30.36 g of triethylamine were added to the solution. Then, 31.50 g of methanesulfonyl chloride were dropped into the solution and stirred for 1 hour. After the reaction was completed, ethyl acetate was added to the reaction mixture, followed by washing with a 2N sulfuric acid, a saturated sodium hydrogen carbonate aqueous solution and a saturated sodium chloride aqueous solution, and dried with sodium sulfate anhydride. The solvent was removed under reduced pressure so as to obtain 78.47 g of (S)-2-[[(3,4-methylenedioxy)phenyl]methyl]-1-acetyloxy-3-methanesulfonyloxypropane.

$^1$H-NMR (400 MHz, CDCl$_3$) δ ppm: 2.08 (s, 3H), 2.27~2.38 (m, 1H), 2.65(d, 2H), 3.01(s, 3H), 4.03(dd, J1=6.6 Hz, J2=11.5 Hz, 1H), 4.11~4.18 (m, 2H), 4.21(dd, J1=4.9 Hz, J2=9.8 Hz, 1H), 5.94 (s, 2H), 6.62 (dd, J1=1.7 Hz, J2=8.6 Hz, 1H), 6.66 (S, 1H), 6.74 (d, J=7.9 Hz, 1H); [α]$_d^{20}$; +3.7° (c=1.02, CHCl$_3$).

REFERENCE EXAMPLE 13

Production of (S)-2-[(4-chlorophenyl)methyl]-1-acetyloxy-3-methanesulfonyloxypropane To 630.7 ml of toluene, 60.68 g of (R)-2-[(4-chlorophenyl)methyl]-3-acetyloxy-1-propanol obtained in Reference example 10 were dissolved. Under ice cooling, 30.36 g of triethylamine were added to the solution. Then, 31.50 g of methanesulfonyl chloride were dropped into the solution and stirred for 1 hour. After the reaction was completed, ethyl acetate was added to the reaction mixture, followed by washing with a 2N sulfuric acid, a saturated sodium hydrogen carbonate aqueous solution and a saturated sodium chloride aqueous solution, and dried with sodium sulfate anhydride. The solvent was removed under reduced pressure so as to obtain 76.19 g of (S)-2-[(4-chlorophenyl)methyl]-1-acetyloxy-3-methanesulfonyloxypropane.

$^1$H-NMR (400 MHz, CDCl$_3$) δ ppm: 2.08 (s, 3H), 2.30~2.42 (m, 1H), 2.71(dd, J1=5.2 Hz, J2=7.6 Hz, 2H), 3.01 (s, 3H), 4.02(dd, J1=6.8 Hz, J2=11.2 Hz, 1H), 4.11~4.19 (m, 2H), 4.21 (dd, J1=4.9 Hz, J2=9.8 Hz, 1H), 7.12 (d, J=8.3 Hz, 2H), 7.29 (d, J=8.3 Hz, 2H); [α]$_d^{20}$; +5.1° (c=1.02, CHCl$_3$).

REFERENCE EXAMPLE 14

Production of (S)-2-benzyl-1-acetyloxy-3-[(p-toluenesulfonyloxy]propane

To 594 ml of methylene chloride, 59.35 g of (R)-2-benzyl-3-acetyloxy-1-propanol (optical purity: 97.6% e.e.) obtained in Reference example 7 were dissolved. To this solution, 30.4 g of triethylamine were added under ice cooling, then, 52.4 g of p-toluenesulfonyl chloride were added to the solution and stirred overnight. After the reaction was completed, ethyl acetate was added to the reaction mixture, followed by washing with a 2N sulfuric acid, a saturated sodium hydrogen carbonate aqueous solution and a saturated sodium chloride aqueous solution, and dried with sodium sulfate anhydride. The solvent was removed under reduced pressure, and 75.20 g of white crystal of (S)-2-benzyl-1-acetyloxy-3-[(p-toluenesulfonyl)oxy]propane was crystallized by n-hexane-ethyl acetate.

Melting point; 67.0~69.0° C.; $^1$H-NMR (400 MHz, CDCl$_3$) δ ppm: 1.96 (s, 3H), 2.21~2.32 (m, 1H), 2.46(s, 3H), 2.64 (dd, J1=4.9 Hz, J2=7.3 Hz, 2H), 3.88~3.99 (m, 2H), 3.99~4.06 (m, 2H), 7.05 (d, J1=16.4 Hz, 2H), 7.15~7.26 (m, 3H), 7.34 (d, J1=8.3 Hz, 2H), 7.77 (d, J1=8.3 Hz, 2H); [α]$_d^{20}$; +5.2° (c=1.01, CHCl$_3$).

REFERENCE EXAMPLE 15

Production of (R)-2-benzyl-1-acetyloxy-3-methanesulfonyloxypropane

The similar reaction of reference example 11 was repeated except that 10.41 g of (S)-2-benzyl-1-acetyloxy-3-propanol obtained in Reference example 8 were used as a starting material, and 13.59 g of (R)-2-benzyl-1-acetyloxy-3-methanesulfonyloxypropane were obtained. The optical purity of the thus obtained (R)-2-benzyl-1-acetyloxy-3-methanesulfonyloxypropane was measured in the same manner as described in Reference example 11.

Optical purity: 98.5% e.e.

EXAMPLE 1

Production of (S)-2-benzyl-3-methanesulfonyloxy-1-propanol

To 120 ml of toluene, 14.31 g of (S)-2-benzyl-1-acetyloxy-3-methanesulfonyloxypropane obtained in Reference example 11 were dissolved. Under ice cooling, 20 ml of ethanol containing 5.39 g of potassium hydroxide were added to this solution and stirred for 2 hours. After the reaction was completed, ethyl acetate was added to the reaction mixture, followed by washing with water and a saturated sodium chloride aqueous solution and dried with sodium sulfate anhydride. The solvent was removed under reduced pressure and a residue was purified with silica gel column chromatography (n-hexane:acetone=1:1) so as to obtain 11.26 g of (S)-2-benzyl-3-methanesulfonyloxy-1-propanol.

IRv cm$^{-1}$; 3550, 2900, 2350, 1495, 1455, 1350, 1175, 1040, 955, 840, 740, 700; $^1$H-NMR(400 MHz, CDCl$_3$) δ ppm: 1.84(br s, 1H), 2.20~2.30(m, 1H), 2.67~2.80(m, 2H), 3.05(s, 3H), 3.66(dd, J1=6.8 Hz, J2=11.2 Hz, 1H), 3.76(dd, J2=11.2 Hz, J3=4.6 Hz, 1H) 4.25(dd, J4=5.6 Hz, J5=10.3 Hz, 1H), 4.36(dd, J5=10.3 Hz, J6=4.4 Hz, 1H), 7.19~7.38 (m, 5H); $[α]_d^{20}$; −22.3° (c=1.02, CHCl$_3$); Optical purity: 98.4% e.e.

The optical purity of (S)-2-benzyl-3-methanesulfonyloxy-1-propanol was determined by the following HPLC conditions:

Column: CHIRALPAK AD (0.45 mm×25 cm)
Eluant; n-hexane: 2-propanol=9:1
Wave length for detection; 254 nm
Elution rate; 1.0 ml/min.
Column temperature; room temperature
Elution time; (R)form:20.2 min., (S)form:17.0 min.

EXAMPLE 2
Production of (R)-2-benzyl-3-methanesulfonyloxy-1-propanol

The similar reaction of Example 1 was repeated except that 14.31 g of (R)-2-benzyl-1-acetyloxy-3-methanesulfonyloxypropane obtained in Reference example 15 were used as a starting material, and 11.15 g of (R)-2-benzyl-3-methanesulfonyloxy-1-propanol were obtained. The optical purity of the thus obtained (R)-2-benzyl-3-methanesulfonyloxy-1-propanol was determined in the same manner as described in Example 1.

$[α]_d^{20}$; +22.2° (c=1.02, CHCl$_3$); Optical purity: 98.4% e.e.

EXAMPLE 3
Production of (S)-2-benzyl-3-methanesulfonyloxy-1-propanol

To 130 ml of methanol, 12.89 g of (S)-2-benzyl-1-acetyloxy-3-methanesulfonyloxypropane obtained in Reference example 11 were dissolved. Under ice cooling, 69 ml of a 2N potassium hydroxide aqueous solution were dropped into the solution and stirred for 1 hour. After the reaction was completed, the solvent was removed under reduced pressure, and ethyl acetate was added, followed by washing with a 1N hydrogen chloride, a saturated sodium hydrogen carbonate aqueous solution and a saturated sodium chloride aqueous solution, and dried with sodium sulfate anhydride. The solvent was removed under reduced pressure and a residue was purified with silica gel column chromatography (n-hexane:acetone=1:1) so as to obtain 11.0 g of (S)-2-benzyl-3-methanesulfonyloxy-1-propanol.

EXAMPLE 4
Production of (S)-2-benzyl-3-methanesulfonyloxy-1-propanol

To 100 ml of toluene, 10.41 g of (R)-2-benzyl-3-acetyloxy-1-propanol obtained in Reference example 7 were dissolved. Under ice cooling, 6.07 g of triethylamine were added to the solution. Then, 6.30 g of methanesulfonyl chloride were dropped into the solution and stirred for 2 hours. Then, 20 ml of ethanol containing 5.67 g of potassium hydroxide were dropped into the solution under ice cooling and stirred for 1 hour. After the reaction was completed, the solution was washed with a saturated sodium chloride aqueous solution and dried with sodium sulfate anhydride. The solvent was removed under reduced pressure so as to obtain 11.30 g of (S)-2-benzyl-3-methanesulfonyloxy-1-propanol.

EXAMPLE 5
Production of (S)-2-[[(3,4-methylenedioxy)phenyl]methyl]-3-methanesulfonyloxy-1-propanol To 330 ml of methanol, 66.07 g of (S)-2-[[(3,4-methylenedioxy)phenyl]methyl]-1-acetyloxy-3-methanesulfonyloxy-propane obtained in Reference example 12 were dissolved. Under ice cooling, 200 ml of a 2N sodium hydroxide aqueous solution were dropped into the solution and stirred for 1 hour. After the reaction was completed, methanol was removed and t-butyl methyl ether was added, followed by washing with a saturated sodium chloride aqueous solution, and dried with sodium sulfate anhydride.

The solvent was removed under reduced pressure so as to obtain 56.51 g of (S)-2-[[(3,4-methylenedioxy)phenyl] methyl]-3-methanesulfonyloxy-1-propanol.

IRv cm$^{-1}$; 3550, 2900, 1610, 1490, 1445, 1350, 1250, 1175, 1100, 1035, 935, 810, 775, 735; $^1$H-NMR(400 MHz, CDCl$_3$) δ ppm: 1.82(br s, 1H), 2.10~2.20(m, 1H), 2.62(dd, J1=5.4 Hz, J2=7.8 Hz, 2H), 3.02(s, 3H), 3.61(dd, J1=6.8 Hz, J2=11.2 Hz, 1H), 3.71(dd, J1=4.4 Hz, J2=10.7 Hz, 1H), 4.21(dd, J1=5.9 Hz, J2=9.8 Hz, 1H), 4.31(dd; J1=4.6 Hz, J2=9.8 Hz, 1H), 5.94(S, 2H), 6.63(d, J=8.3 Hz, 1H), 6.68(S, 1H), 6.74 (d, J=9.9Hz, 1H); $[α]_d^{20}$; −21.6° (c=1.02, CHCl$_3$).

EXAMPLE 6
Production of (S)-2-[(4-chlorophenyl)methyl]-3-methanesulfonyloxy-1-propanol To 330 ml of methanol, 64.16 g of (S)-2-[(4-chlorophenyl)methyl]-1-acetyloxy-3-methanesulfonyloxypropane obtained in Reference example 13 were dissolved. Under ice cooling, 200 ml of a 2N sodium hydroxide aqueous solution were dropped into the solution and stirred for 1 hour. After the reaction was completed, methanol was removed and t-butyl methyl ether was added, followed by washing with a saturated sodium chloride aqueous solution and dried with sodium sulfate anhydride. The solvent was removed under reduced pressure. By crystallization using t-butyl methyl ether-cyclohexane, 54.64 g of white crystal of (S)-2-[(4-chlorophenyl)methyl]-3-methanesulfonyloxy-1-propanol were obtained.

Melting point; 69.0~71.0° C.; IRvcm$^{-1}$; 3550, 2850, 1490, 1330, 1160, 1105, 1060, 960, 895, 845, 790, 755; $^1$H-NMR(400 MHz, CDCl$_3$) δ ppm: 1.95(br s, 1H), 2.12~2.22(m, 1H), 2.67(dd, J1=5.4 Hz, J2=7.3 Hz, 2H), 3.02(s, 3H), 3.59(dd, J1=6.6 Hz, J2=11.0 Hz, 1H), 3.70(dd, J1=4.2 Hz, J2=11.0 Hz, 1H), 4.20(dd, J1=5.6 Hz, J2=10.0 Hz, 1H), 4.29(dd, J1=4.4 Hz, J2=9.8 Hz, 1H), 7.13(d, J=8.3 Hz, 2H), 7.28(d, J=8.3Hz, 2H); $[α]_d^{20}$; −26.9° (c=1.01, CHCl$_3$).

REFERENCE EXAMPLE 16
Production of (S)-2-benzyl-3-(p-toluenesulfonyl)oxy-1-propanol To 362 ml of methanol, 72.49 g of (S)-2-benzyl-1-acetyloxy-3-[(p-toluenesulfonyl)oxy]propane obtained in Reference example 14 were dissolved. Under ice cooling, 200 ml of a 2N sodium hydroxide aqueous solution were dropped into the solution and stirred for 1 hour. After the reaction was completed, methanol was removed and t-butyl methyl ether was added, followed by washing with a saturated sodium chloride aqueous solution and dried with sodium sulfate anhydride. The solvent was removed under reduced pressure.

By crystallization using t-butyl methyl ether-cyclohexane, 58.5 g of white crystal of (S)-2-benzyl-3-(p-toluenesulfonyl)oxy-1-propanol were obtained.

Melting point; 57.0~59.0° C.; IRv cm$^{-1}$; 3400, 2900, 1600, 1490, 1465, 1355, 1175, 1095, 1055, 1005, 920, 815, 750, 700, $^1$H-NMR(400 MHz, CDCl$_3$) δ ppm: 1.73(br s, 1H), 2.05~2.15(m, 1H), 2.45(s, 3H), 2.54~2.68(m, 2H), 3.57(dd, J1=6.6 Hz, J2=10.5 Hz, 1H), 3.65(dd, J1=4.6 Hz, J2=11.0 Hz, 1H), 4.00(dd, J1=5.4 Hz, J2=9.8 Hz, 1H); 4.10(dd, J1=4.4Hz, J2=9.8 Hz, 1H), 7.08(d, J=7.3 Hz, 2H), 7.14~7.28(m, 2H), 7.34(d, J=8.3 Hz, 1H), 7.78(d, J=7.8 Hz, 1H); $[α]_d^{20}$; −18.8° (c=1.02, MeOH).

EXAMPLE 7
Production of (R)-2-benzyl-3-methanesulfonyloxypropionic Acid

To 50 ml of toluene, 6.41 g of (S)-2-benzyl-3-methanesulfonyloxy-1-propanol obtained in Example 1 were dissolved. To this solution, 45.2 mg of 4-hydroxy-2,2,6,6-tetramethylpiperidine-1-oxy, 5.30 ml of a 0.5M potassium bromide aqueous solution and 2.62 ml of a 0.5M trioctylmethylammonium chloride-toluene solution were added and stirred under ice cooling. To this reaction mixture, 48.8 ml of a sodium hypochlorite solution saturated with sodium hydrogen carbonate were added and vigorously stirred for 0.5 hour under ice cooling. After the reaction was completed, a water layer was recovered. To this water layer, toluene and a 2N sulfuric acid were added and the toluene layer was recovered. The toluene layer was washed with a 1N hydrochloric acid and a saturated sodium chloride aqueous solution and dried with sodium sulfate anhydride. The solvent was removed under reduced pressure and a residue was purified with silica gel column chromatography (n-hexane: acetone: acetic acid=60:40:1) so as to obtain 4.98 g of white crystal of (R)-2-benzyl-3-methanesulfonyloxypropionic acid.

Melting point; 70.0~72.0° C.; IRv cm$^{-1}$; 3025, 2350, 1700, 1455, 1345, 1175, 975, 800, 740, 700; $^1$H-NMR(400 MHz, CDCl$_3$) δ ppm: 2.15~2.95(m, 1H), 2.99(s, 3H), 3.08~3.18(m, 2H) 4.31(d, J=5.4Hz, 2H), 7.12~7.36(m, 5H) 9.50(br s, 1H); $[α]_d^{20}$; −12.6° (c=1.01, CHCl$_3$); Optical purity: 98.2% e.e.

The optical purity of (R)-2-benzyl-3-methanesulfonyloxy-propionic acid was determined by the following HPLC conditions:

Column: CHIRALPAK AD(0.45 mm×25 cm)

Eluant; n-hexane: 2-propanol: trifluoroacetic acid= 900:100:1

Wave length for detection; 254 nm

Elution rate; 1.0 ml/min.

Column temperature; room temperature

Elution time; (R)form:27.7 min., (S)form:19.1 min.

EXAMPLE 8
Production of (S)-2-benzyl-3-methanesulfonyloxypropionic Acid

The similar reaction of Example 7 was repeated except that 6.41 g of (R)-2-benzyl-3-methanesulfonyloxy-1-propanol obtained in Example 2 were used as a starting material, and 4.91 g of white crystal of (S)-2-benzyl-3-methanesulfonyloxypropionic acid were obtained. The optical purity of the thus obtained (S)-2-benzyl-3-methanesulfonyloxypropionic acid was measured in the same manner as described in Example 7.

$[α]_d^{20}$; +12.7° (c=1.01, CHCl$_3$); Optical purity: 98.2% e.e.

EXAMPLE 9
Production of (R)-2-benzyl-3-methanesulfonyloxypropionic Acid

To 48.9 ml of acetone, 4.89 g of (S)-2-benzyl-3-methanesulfonyloxy-1-propanol obtained in Example 1 were dissolved. Into this solution, Jones reagent was dropped under ice cooling. After the reaction was completed, excessive Jones reagent was decomposed by adding isopropyl alcohol and the solvent was removed. A residue was dissolved in ethyl acetate, washed with a saturated sodium chloride aqueous solution and dried with sodium sulfate anhydride. The solvent was removed under reduced pressure and the residue was purified with silica gel column chromatography (n-hexane:ethyl acetate:acetic acid=40:80:1) so as to obtain 3.60 g of white crystal of (R)-2-benzyl-3-methanesulfonyloxy-propionic acid.

EXAMPLE 10
Production of (R)-2-[[(3,4-methylenedioxy)phenyl]methyl]-3-methanesulfonyloxypropionic Acid To 50.0 ml of acetone, 5.00 g of (S)-2-[[(3,4-methylenedioxy)phenyl]methyl]-3-methanesulfonyloxy-1-propanol obtained in Example 5 were dissolved. Into this solution, Jones reagent was dropped under ice cooling. After the reaction was completed, excessive Jones reagent was decomposed by adding isopropyl alcohol and the solvent was removed under reduced pressure. Tertiary butyl methyl ether and distilled water were added to the residue. After stirring, a t-butyl methyl ether layer was recovered and a saturated sodium hydroxide aqueous solution was added thereto and stirred. The water layer was recovered and t-butyl methyl ether was added thereto. Into this solution, a 6N sulfuric acid was dropped under ice cooling so that the water layer became acidic. The t-butyl methyl ether layer was recovered and washed with a saturated sodium chloride aqueous solution and dried with sodium sulfate anhydride. The solvent was removed under reduced pressure and the residue was purified with silica gel column chromatography (n-hexane:ethyl acetate:acetic acid=100:100:1) so as to obtain 3.50 g of white crystal of (R)-2-[[(3,4-methylenedioxy)phenyl]methyl]-3-methanesulfonyloxypropionic acid.

IRv cm$^{-1}$; 2950, 2750, 1715, 1610, 1490, 1445, 1355, 1250, 1175, 1100, 1035, 965, 815, 730; $^1$H-NMR(400 MHz, CDCl$_3$) δ ppm: 2.75~2.90(m, 1H), 3.02(s, 3H), 3.05~3.15 (m, 2H) 4.32(d, J=4.9Hz, 2H), 5.95(s, 2H), 6.65(dd, J1=2.0 HZ, J2=7.8 Hz, 1H), 6.68(d, J=2.0 Hz, 1H), 6.75(d, J=7.8 Hz, 1H); $[α]_d^{20}$; −9.0° (c=1.02, CHCl$_3$).

EXAMPLE 11
Production of (R)-2-[(4-chlorophenyl)methyl]-3-methanesulfonyloxy-propionic Acid To 100.0 ml of acetone, 10.00 g of (S)-2-[(4-chlorophenyl)methyl]-3-methanesulfonyloxy-1-propanol obtained in Example 6 were dissolved. Into this solution, Jones reagent was dropped under ice cooling. After the reaction was completed, excessive Jones reagent was decomposed by adding isopropyl alcohol, and the solvent was removed under reduced pressure. Tertiary butyl methyl ether and distilled water were added to the residue. After stirring, t-butyl methyl ether layer was recovered and a saturated sodium hydroxide aqueous solution was added thereto and stirred. The water layer was recovered and t-butyl methyl ether was added thereto. Into this solution, a 6N sulfuric acid was dropped under ice cooling so that the water layer became acidic. The t-butyl methyl ether layer was recovered, washed with a saturated sodium chloride aqueous solution and dried with sodium sulfate anhydride. The solvent was removed under reduced pressure. By crystallization using t-butyl methyl ether-cyclohexane, 6.20 g of white crystal of (R)-2-[(4-chlorophenyl)methyl]-3-methanesulfonyloxypropionic acid were obtained.

Melting point: 107.0~109.0° C.; IRv cm$^{-1}$; 3025, 2650, 1700, 1495, 1415, 1345, 1225, 1175, 1090, 990, 965, 910, 890, 815, 725; $^1$H-NMR(400 MHz, CDCl$_3$) δ ppm: 2.80~2,94(m, 1H), 3.02(s, 3H), 3.05~3.15(m, 2H) 4.32(d, J=5.4 Hz, 2H), 7.i5(d, J=8.3 Hz, 2H), 7.30(d, J=8.3 Hz, 2H); $[\alpha]_d^{20}$; −4.2° (c=1.00, CHCl$_3$).

EXAMPLE 12
Production of (R)-2-benzyl-3[(p-toluenesulfonyl)oxy] propionic Acid To 20.0 ml of acetone, 2.00 g of (S)-2-benzyl-3-(p-toluenesulfonyl)oxy-1-propanol obtained in Reference example 16 were dissolved. Into this solution, Jones reagent was dropped under ice cooling. After the reaction was completed, excessive Jones reagent was decomposed by adding isopropyl alcohol, and the solvent was removed under reduced pressure. Tertiary butyl methyl ether and distilled water were added to the residue. After stirring, the t-butyl methyl ether layer was recovered and a saturated sodium hydroxide aqueous solution was added thereto and stirred. The water layer was recovered and t-butyl methyl ether was added thereto. To this solution, a 6N sulfuric acid was dropped under ice cooling so that the water layer became acidic. The t-butyl methyl ether layer was recovered, washed with a saturated sodium chloride aqueous solution and dried with sodium sulfate anhydride. The solvent was removed under reduced pressure. By crystallization using t-butyl methyl ether-cyclohexane, 1.23 g of white crystal of (R)-2-benzyl-3- [(p-toluenesulfonyl)oxy] propionic acid were obtained.

Melting point: 103.0~105.0° C.; IRv cm$^{-1}$; 3000, 2600, 1705, 1600, 1495, 1455, 1425, 1355, 1270, 1180, 1095, 980, 930, 815; $^1$H-NMR(400 MHz, CDCl$_3$) δ ppm: 2.45(s, 3H), 2.78~2.90(m, 1H), 2.95~3.07(m, 2H) 4.12(d, J=5.4 Hz, 2H), 7.08(dd, J1=1.7 Hz, J2=7.6 Hz, 2H), 7.20~7.30(m, 3H), 7.32(d, J=8.3 Hz, 2H), 7.75(d, J=8.3 Hz, 2H), 8.70 (br s, 1H); $[\alpha]_d^{20}$; −8.3 ° (c=1.01, CHCl$_3$).

REFERENCE EXAMPLE 17
Production of (R)-2-benzyl-3-hydroxypropionic Acid

To 10 ml of acetone, 590 mg of (S)-2-benzyl-3-acetyloxy-1-propanol obtained in Reference example 8 were dissolved. Into this solution, Jones reagent was dropped under ice cooling. After stirring at room temperature for 2 hours, excessive Jones reagent was decomposed by adding isopropyl alcohol, and the solvent was removed under reduced pressure. The residue was dissolved in ethyl acetate, washed with a saturated sodium chloride aqueous solution and dried with sodium sulfate anhydride. The solvent was removed under reduced pressure and the residue was dissolved in 10 ml of methanol. To this solution, 8 ml of a 1N potassium carbonate aqueous solution were added under ice cooling and stirred overnight at room temperature. After the reaction was completed, the solvent was removed under reduced pressure. To a residue, ethyl acetate was added, washed with a 1N hydrogen chloride and a saturated sodium chloride aqueous solution and dried with sodium sulfate anhydride. The solvent was removed under reduced pressure and the residue was re-crystallized by ether-n-hexane so as to obtain 305 mg of white crystal of (R)-2-benzyl-3-hydroxypropionic acid.

Melting point,; 67.5~68.5° C.; $^1$H-NMR(400 MHz, CDCl$_3$) δ ppm: 2.75~2.93(m, 2H), 2.97~3.13(m, 1H) 3.60~3.85(m, 2H) 5.14(br s, 2H), 7.06~7.34(m, 5H); $[\alpha]_d^{20}$; +13.9° (c=0.97, CHCl$_3$); Optical purity: 98.0% e.e.

The optical purity of (R)-2-benzyl-3-hydroxypropionic acid was determined by the following HPLC conditions:

Column: CHIRALPAK AD(0.45 mm×25 cm)

Eluant; n-hexane: 2-propanol: trifluoroacetic acid= 1000:40:1

Wave length for detection; 254 nm

Elution rate; 0.5 ml/min.

Column temperature; room temperature

Elution time; (R)form:61.6 min., (S)form:58.8 min.

REFERENCE EXAMPLE 18
Production of (S)-2-benzyl-3-hydroxypropionic Acid

The similar reaction of Reference Example 17 was repeated except that 590 mg of (R)-2-benzyl-3-acetyloxy-1-propanol obtained in Reference example 7 were used as a starting material, and 301 mg of white crystal of (S)-2-benzyl-3-hydroxypropionic acid were obtained. The optical purity of the thus obtained (S)-2-benzyl-3-hydroxypropionic acid was determined in the same manner as described in Reference example 17.

$[\alpha]_d^{20}$; −13.9° (c=0.97, CHCl$_3$); Optical purity: 98.5% e.e.

EXAMPLE 13
Production of (R)-2-benzyl-3-methanesulfonyloxypropionic Acid

To 1.8 ml of ethyl acetate, 180 mg of (R)-2-benzyl-3-hydroxypropionic acid obtained in Reference example 17 were dissolved. To this solution, 202 mg of triethylamine were added. Under ice cooling, 126 mg of methanesulfonyl chloride were dropped, and stirred overnight at room temperature. After the reaction was completed, ethyl acetate was added, washed with a 1N hydrogen chloride, a saturated sodium hydrogen carbonate aqueous solution and a saturated sodium chloride aqueous solution and dried with sodium sulfate anhydride. The solvent was removed under reduced pressure, followed by purifying the residue with silica gel column chromatography (n-hexane; ethyl acetate; acetic acid=40:60:1), thereby obtaining 230 mg of white crystal of (R)-2-benzyl-3-methanesulfonyloxypropionic acid.

EXAMPLE 14
Production of (S)-2-benzyl-3-methanesulfonyloxypropionic Acid

The similar reaction of Example 13 was repeated except that 180.2 mg of (S)-2-benzyl-3-hydroxypropionic acid obtained in Reference example 18 were used as a starting material, and 228 mg of white crystal of (S)-2-benzyl-3-methanesulfonyloxypropionic acid were obtained.

EXAMPLE 15
Production of (S)-2-benzyl-3-acetylthiopropionic Acid

To 2 ml of methanol, 228 mg of sodium methoxide were suspended. Into this suspension, 305 mg of thioacetic acid were dropped and stirred for 30 min. at room temperature. To this solution, 7.5 ml of a methanol solution containing 517 mg of (R)-2-benzyl-3-methanesulfonyloxypropionic acid obtained in Example 7 were added and stirred overnight at room temperature. After the reaction was completed, water was added and methanol was removed under reduced pressure. Ethyl acetate was added and washed with a 1N hydrogen chloride and a saturated sodium chloride aqueous solution. After drying with sodium sulfate anhydride, the solvent was removed under reduced pressure, followed by purifying the residue with silica gel column chromatography (n-hexane:acetone:acetic acid=70:30:1), thereby obtaining 410 mg of (S)-2-benzyl-3-acetylthiopropionic acid.

$^1$H-NMR(400 MHz, CDCl$_3$) δ ppm: 2.33(s, 3H), 2.87~3.16(m, 5H), 7.14~7.34(m, 5H) 9.00(br s, 1H); $[\alpha]_d^{20}$; +36.1° (c=1.00, MeOH); Optical purity: 98.2% e.e.

The optical purity of (S)-2-benzyl-3-acetylthiopropionic acid was determined by the following HPLC conditions:

Column: CHIRALPAK AD(0.45 mm×25 cm)

Eluant; n-hexane: 2-propanol: trifluoroacetic acid= 90:10:1

Wave length for detection; 254 nm

Elution rate; 0.5 ml/min.

Column temperature; room temperature

Elution time; (R)form:18.2 min., (S)form:20.9 min.

EXAMPLE 16

Production of (R)-2-benzyl-3-acetylthiopropionic Acid

The similar reaction of Example 15 was repeated except that 517 mg of (S)-2-benzyl-3-methanesulfonyloxypropionic acid obtained in Example 8 were used as a starting material, and 408 mg of (R)-2-benzyl-3-acetylthiopropionic acid were obtained. The optical purity of the thus obtained (R)-2-benzyl-3-acetylthiopropionic acid was determined in the same manner as described in Example 15.

$[\alpha]_d^{20}$; −36.1° (c=1.00, MeOH); Optical purity: 98.1% e.e.

EXAMPLE 17

Production of (S)-2-benzyl-3-acetylthiopropionic Acid

To 1.5 ml of methanol, 405 mg of triethylamine were dissolved. Into this solution, 305 ml of thioacetic acid were dropped and stirred for 30 min. at room temperature. To this solution, 2.2 ml of a methanol solution containing 517 mg of (R)-2-benzyl-3-methanesulfonyloxypropionic acid obtained in Example 7 were added and stirred overnight at room temperature. After the reaction was completed, water was added and methanol was removed under reduced pressure. Ethyl acetate was added and washed with a 1N hydrogen chloride and a saturated sodium chloride aqueous solution. After drying with sodium sulfate anhydride, the solvent was removed under reduced pressure, followed by purifying the residue with silica gel column chromatography (n-hexane:acetone:acetic acid=70:30:1), thereby obtaining 396 mg of (S)-2-benzyl-3-acetylthiopropionic acid.

EXAMPLE 18

Production of (S)-2-benzyl-3-acetylthiopropionic Acid

To 10 ml of methanol, 3.00 g of potassium carbonate were suspended. To this suspension, 1.65 g of thioacetic acid were dropped and stirred for 30 min. under ice cooling. To this solution, 26.5 ml of a methanol solution containing 4.65 g of (R)-2-benzyl-3-methanesulfonyloxypropionic acid obtained in Example 7 were added and stirred for 18 hours at room temperature. After the reaction was completed, water was added and methanol was removed under reduced pressure. Ethyl acetate was added and washed with a 1N hydrogen chloride and a saturated sodium chloride aqueous solution. After drying with sodium sulfate anhydride, the solvent was removed under reduced pressure, followed by purifying the residue with silica gel column chromatography (n-hexane:acetone:acetic acid=70:30:1), thereby obtaining 3.83 g of (S)-2-benzyl-3-acetylthiopropionic acid.

EXAMPLE 19

Production of (S)-2-benzyl-3-acetylthiopropionic Acid

To 3.0 ml of methanol, 508 mg of potassium thioacetate were suspended and stirred for 30 min. at room temperature. To this solution, 2.2 ml of a methanol solution containing 517 mg of (R)-2-benzyl-3-methanesulfonyloxypropionic acid obtained in Example 7 were added and stirred overnight at room temperature. After the reaction was completed, water was added and methanol was removed under reduced pressure. Ethyl acetate was added and washed with a 1N hydrogen chloride and a saturated sodium chloride aqueous solution. After drying with sodium sulfate anhydride, the solvent was removed under reduced pressure, followed by purifying the residue with silica gel column chromatography (n-hexane:acetone:acetic acid=70:30:1), thereby obtaining 401 mg of (S)-2-benzyl-3-acetyithiopropionic acid.

Industrial Applicability

An optical active 2-aralkyl-3-sulfonyloxy-1-propanol and an optical active 2-aralkyl-3-sulfonyloxypropionic acid, which are sulfonic acid ester derivatives, produced according to the present invention are novel. These compounds can be produced in an industrial scale with high yield using as a raw material an optical active 2-aralkyl-3-acyloxy-1-propanol, which is easy to be produced. Furthermore, an optical active 2-aralkyl-3-sulfonyloxypropionic acid can be converted easily into an optical active 2-aralkyl-3-thiopropionic acid, which is an important intermediate of enkephalinase inhibitor, by reacting with a thio-compound.

What is claimed is:

1. An optical active 2-aralkyl-3-sulfonyloxy-1-propanol having the following general formula (1):

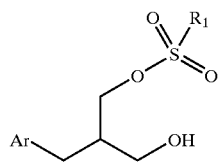

(1)

wherein Ar is an aryl group that may be substituted and R$_1$ is methyl group, ethyl group, n-propyl group, isopropyl group, benzyl group, p-chlorophenyl group, p-bromophenyl group, p-methoxyphenyl group, o-nitrophenyl group, m-nitrophenyl group, p-nitrophenyl group or 1-naphthyl group.

2. The optical active 2-aralkyl-3-sulfonyloxy-1-propanol according to claim 1, wherein Ar is a phenyl group that may be substituted or a naphthyl group that may be substituted.

3. The optical active 2-aralkyl-3-sulfonyloxy-1-propanol according to claim 1, wherein Ar is a phenyl group that may be substituted with alkyl group, substituted alkyl group, alkoxy group, substituted alkoxy group or halogen atom.

4. The optical active 2-aralkyl-3-sulfonyloxy-1-propanol according to claim 1, wherein Ar is a phenyl group.

5. The optical active 2-aralkyl-3-sulfonyloxy-1-propanol according to claim 1, 2, 3 or 4, wherein R$_1$ is a methyl group.

6. The optical active 2-aralkyl-3-sulfonyloxy-1-propanol according to claim 1, wherein Ar is a phenyl group and R$_1$ is a methyl group.

7. A method for producing an optical active 2-aralkyl-3-sulfonyloxy-1-propanol having the following general formula (1):

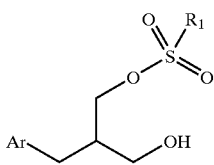

(1)

wherein Ar is an aryl group that may be substituted and $R_1$ is an alkyl group that may be substituted or an aryl group that may be substituted, which comprises hydrolyzing, in the presence of a base, an optical active 2-aralkyl-1-acyloxy-3-sulfonyloxypropane having the following general formula (2):

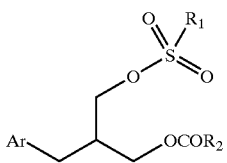

(2)

wherein Ar is an aryl group that may be substituted, $R_1$ is an alkyl group that may be substituted or an aryl group that may be substituted and $R_2$ is a linear or branched alkyl group that may be substituted, a linear or branched alkenyl group that may be substituted or an aryl group that may be substituted.

8. The method according to claim 7, wherein Ar is a phenyl group that may be substituted or a naphthyl group that may be substituted.

9. The method according to claim 7, wherein Ar is a phenyl group that may be substituted with alkyl group, substituted alkyl group, alkoxy group, substituted alkoxy group or halogen atom.

10. The method according to claim 7, wherein Ar is a phenyl group.

11. The method according to claim 7, 8, 9 or 10, wherein $R_1$ is methyl group, ethyl group, n-propyl group, isopropyl group, benzyl group, p-chlorophenyl group, p-bromophenyl group, p-methoxyphenyl group, o-nitrophenyl group, m-nitrophenyl group, p-nitrophenyl group or 1-naphthyl group.

12. The method according to claim 7, 8, 9 or 10, wherein $R_1$ is a methyl group.

13. The method according to claim 7, wherein Ar is a phenyl group and $R_1$ is a methyl group.

\* \* \* \* \*